United States Patent [19]

Legg

[11] 4,343,705

[45] Aug. 10, 1982

[54] BIOLOGICAL LIQUID FRACTIONATION USING ALTERNATE OPPOSITE FLOW DIRECTIONS ACROSS A MEMBRANE

[75] Inventor: Kenneth D. Legg, Wellesley, Mass.

[73] Assignee: Instrumentation Laboratory, Lexington, Mass.

[21] Appl. No.: 202,478

[22] Filed: Oct. 31, 1980

[51] Int. Cl.³ .................. B01D 13/00; B01D 31/00
[52] U.S. Cl. .................. 210/637; 210/651; 210/805; 210/195.2; 210/257.2; 210/422; 210/433.2; 210/443; 210/445
[58] Field of Search ............. 210/195.1, 195.2, 257.2, 210/258, 321, 409, 416.1, 422, 433.2, 433 M, 436, 443, 445, 472, 927, 637, 650, 651, 779, 805; 422/101

[56] References Cited

U.S. PATENT DOCUMENTS

| | | | |
|---|---|---|---|
| 3,211,645 | 10/1965 | Ferrari | 210/22 |
| 3,489,145 | 1/1970 | Judson et al. | 120/214 |
| 3,556,302 | 1/1971 | Agranat | 210/445 X |
| 3,567,031 | 3/1971 | Loeffler | 210/312 |
| 3,705,100 | 12/1972 | Blatt et al. | 210/23 |
| 4,001,117 | 1/1977 | Trechsel | 210/180 |
| 4,189,385 | 2/1980 | Greenspan | 210/136 |
| 4,191,182 | 3/1980 | Popovich et al. | 128/214 R |
| 4,212,742 | 7/1980 | Solomon et al. | 210/247 |

Primary Examiner—Peter A. Hruskoci
Assistant Examiner—David R. Sadowski

[57] ABSTRACT

A fractionation system for providing a clarified fraction or a fraction for analysis of biological fluids and the like includes a disposable filtration vessel with a first reservoir chamber adapted to receive the fluid to be fractionated, a second reservoir chamber and a flow channel that extends between the reservoir chambers. The lower surface of the flow channel is defined by a microporous sheet membrane, and collection structure is disposed on the side of the membrane opposite the flow channel. Low gas pressure (less than ten psi) applied alternately to liquid surfaces in the reservoir chambers produced reciprocating flow of the fluid between the reservoir chambers in a wide thin stream through the flow channel with resulting collection of a fraction of the liquid material that passes through the membrane. A one-half milliliter volume of plasma from a two milliliter volume sample of blood is obtained with the system in less than one minute without any discernible hemolysis.

13 Claims, 11 Drawing Figures

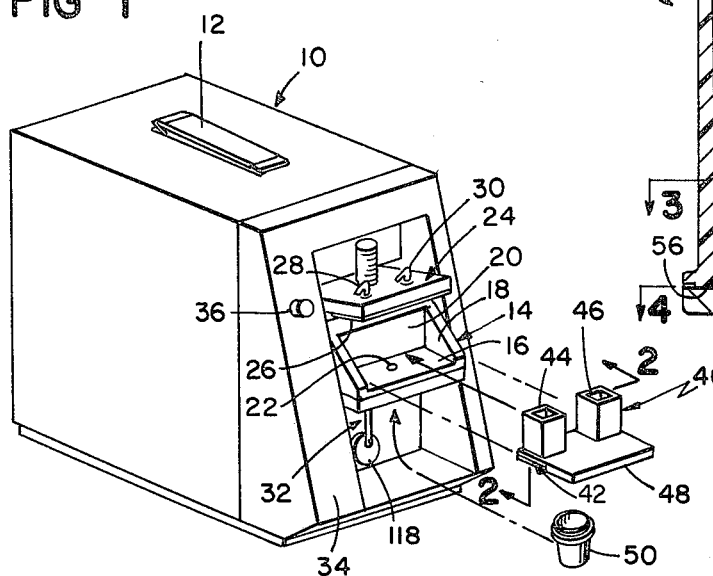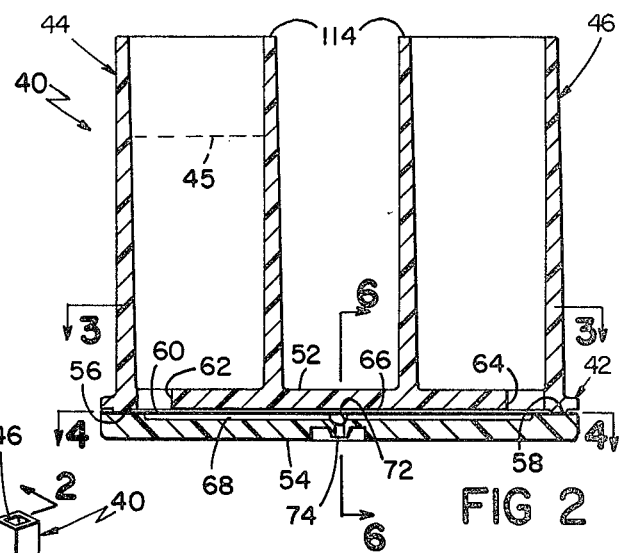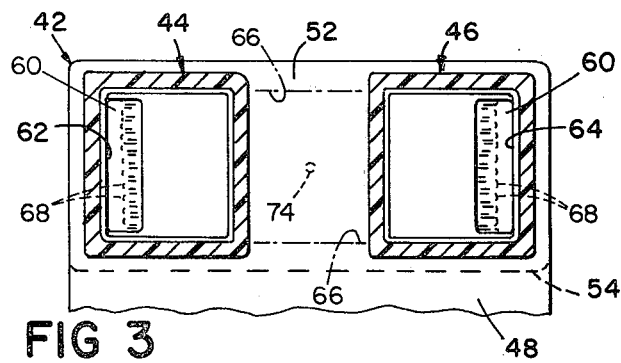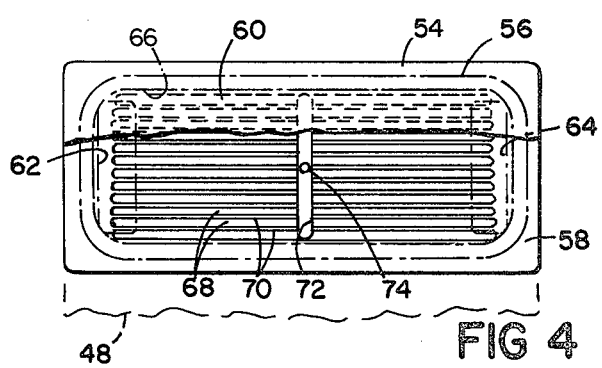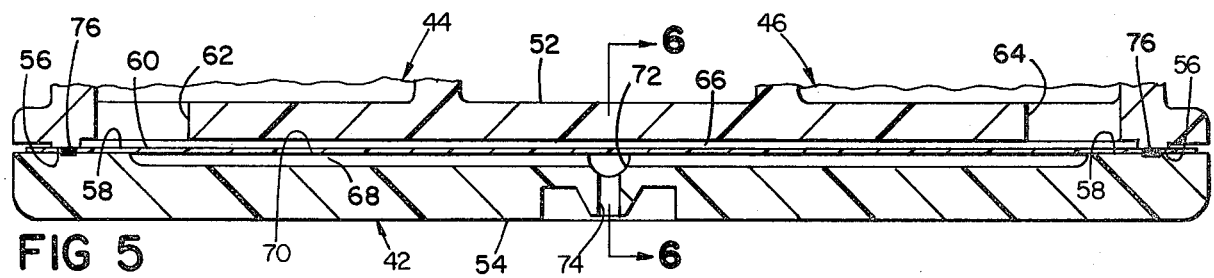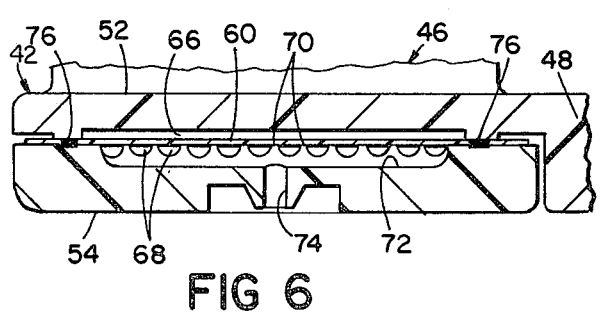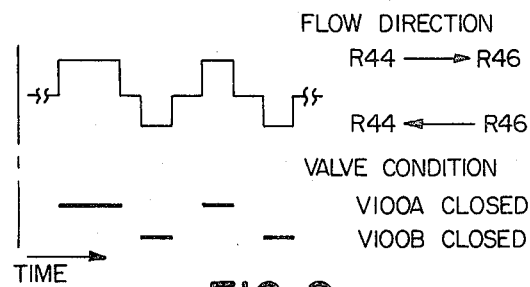

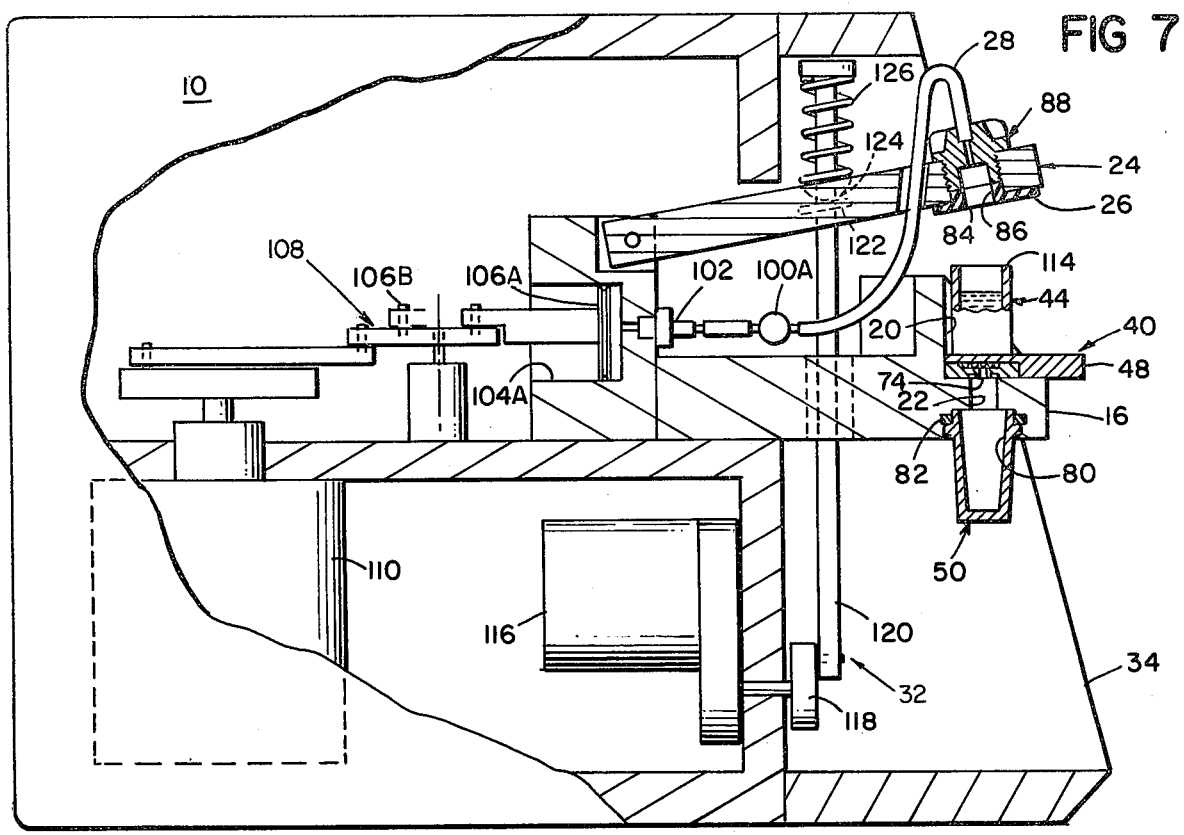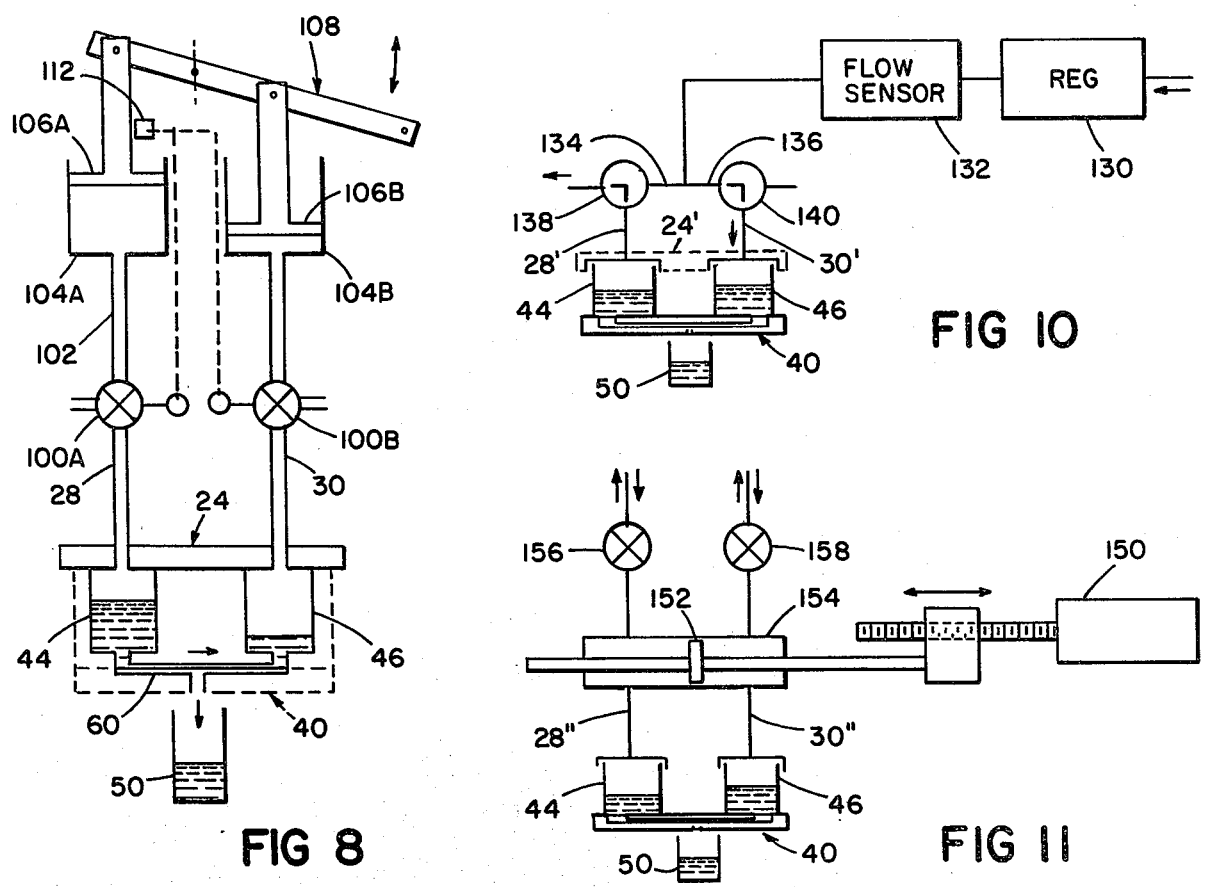

BIOLOGICAL LIQUID FRACTIONATION USING ALTERNATE OPPOSITE FLOW DIRECTIONS ACROSS A MEMBRANE

This invention relates to fractionation systems and more particularly to systems particularly useful for fractionating biological fluids and the like.

It is frequently desired to fractionate blood, for example, to obtain a plasma fraction for analysis. Approximately forty-five percent of the volume of blood is in the form of cellular components, those cellular components including red blood cells (also referred to as erythrocytes), white blood cells (also referred to as leukocytes), and platelets. Plasma makes up the remaining volume of blood, and basically it is the fluid portion of the blood which suspends the cellular components and comprises a solution of approximately ninety percent water, seven percent protein, and three percent of various other organic and inorganic solutes. A basic problem in the fractionation of blood arises from fact that many of the cellular components are fragile and easily destroyed.

Numerous fractionation processes and apparatuses have been proposed, including techniques based upon the reversible agglomeration of blood cells in the presence of carbohydrates, techniques using various centrifugation procedures, and utltrafiltration techniques. Most of the known fractionation processes and apparatuses are either elaborate and therefore expensive or require relatively large quantities of liquid for operation, or both. In general, such processes also require particular operator skills and training. Among problems encounted in processes for the ultrafiltration of blood are the possibility of irreversible damage or hemolysis of the cells, occlusion of the filter membrane pores, and relatively long periods of fractionation time required for the collection of cell-free plasma.

In accordance with the invention there is provided a fractionation system that enables fractionation of biological fluids and the like to provide a fraction for analysis or a clarified fraction. The fractionation system includes a filtration vessel that has a first reservoir chamber adapted to receive the liquid material to be fractionated, a second reservoir chamber and a flow channel that extends between the reservoir chambers. One surface of the flow channel is defined by a microporous membrane, and collection structure is disposed on the side of the membrane opposite the flow channel. Each reservoir chamber has coupling structure for connection to a pressure source that includes means for applying gas pressure alternately to the reservoir chambers for producing reciprocating flow of the liquid material between the reservoir chambers through the flow channel with resulting flow of a fraction of the liquid material through the membrane and the collection structure.

In a preferred embodiment the system includes a disposible filtration vessel that has a body portion defining the flow channel with ports at opposite ends of the channel and two reservoir chambers that are integral with the body portion. Preferably the flow channel forms the liquid material to be fractionated into a wide thin sheet (the depth of the flow channel being less than 0.3 millimeters and the width of the flow channel being at least twenty times its depth). The filter membrane has multiple pores, each less than one micron in dimension.

In a particular embodiment, the filtration vessel includes a base plate with two integral reservoir chambers upstanding therefrom, and with a flow channel recess in the lower surface of the base plate. A reservoir port in the bottom of each reservoir chamber provides flow communication with the corresponding end of the flow channel recess and is of substantially the same width as the flow channel recess. A sheet microporous membrane is seated on the lower surface of the base plate and forms the lower surface of the flow channel, and is held in position by a cover plate member that includes an array of longitudinally extending collection channels for conveying the fraction of liquid material that passes through the membrane to a collection passage. The two coupling ports of the reservoir chambers are disposed in a plane at the top of the chambers, the open top of one of the chambers being arranged for convenient introduction of the liquid to be fractionated into that chamber. The filtration vessel is seated on a support platform of fractionation apparatus which includes an arrangement for coupling gas pressure supply conduits to the open top surfaces of the reservoir chambers; and air pressure is applied alternately through those conduits to the surface of liquid in the reservoir chambers to produce reciprocating flow of liquid material through the flow channel. In particular embodiments, a vent valve is provided in each gas pressure supply conduit and the system is arranged to operate those vent valves alternately. The gas pressure differential applied to the reservoir chambers is less than ten psi, and preferably one reservoir chamber is always vented to atmosphere.

The invention provides rapid fractionation of blood with alternating flow across the filter membrane by application of pressure at a gas-liquid interface such that a one-half milliliter volume of plasma may be obtained from a two milliliter volume sample of blood in less than one minute without discernible hemolysis. The invention provides easy, quick, and convenient fractionation of biological fluids in a system which may utilize disposable sample handling filtration vessels, eliminating need for a cleaning step between fractionation of successive samples of biological fluids; and requiring minimal operator skill and process supervision.

Other features and advantages will be seen as the following description of particular embodiments progresses, in conjunction with the drawings, in which:

FIG. 1 is a perspective view of a plasma separation system in accordance with the invention;

FIG. 2 is a sectional view taken along the line 2—2 of FIG. 1 of the plasma separation cartridge used in the system shown in FIG. 1;

FIG. 3 is a sectional view taken along the line 3—3 of FIG. 2;

FIG. 4 is a sectional view taken along the line 4—4 of FIG. 2, with portions of membrane 60 broken away;

FIG. 5 is an enlarged sectional view showing further details of the flow channel in the cartridge shown in FIG. 2;

FIG. 6 is a sectional view taken along the line 6—6 of FIG. 5;

FIG. 7 is a side view, with parts broken away, of the plasma separation apparatus shown in FIG. 1 with a plasma separation cartridge and collection cup received on the support platform;

FIG. 8 is a diagrammatic view illustrating operation of the fractionation system shown in FIG. 1;

FIG. 9 is a diagram illustrating timing aspects of the alternating direction of flow between reservoirs 44 and 46; and the corresponding intervals when vent valves 100A and 100B are closed; and FIGS. 10 and 11 are diagrammatic views illustrating two further fractionation arrangements.

DESCRIPTION OF PARTICULAR EMBODIMENTS

With reference to FIG. 1, the plasma separation system includes an instrument (which may be battery-powered) that has a housing 10 with carrying handle 12. Mounted on the front face of housing 10 is cartridge receiving structure 14 that includes a support platform 16, and aligning side walls 18 and rear wall 20. Flow passage 22 extends through platform 16. Disposed above cartridge receiving structure 14 is a coupling plate 24 which carries on its lower surface seal members 26, and has extending from its upper surface air supply conduits 28 and 30. Coupling plate 24 is mounted for pivoting movement between a raised (open) position and a lower (coupling) position as moved by drive linkage 32. Cowl structure 34 on the front wall of housing 10 surrounds cartridge receiving structure 14. Depression of operating switch 36 on the front face of cowl 34 initiates a fractionation sequence.

Disposable fractionation cartridge 40 includes body structure 42 which is dimensioned to be positioned on platform 16 by engagement with side walls 18 and rear wall 20 so that an integral discharge passage 74 is aligned with passage 22. Integral with body structure 42 are two upstanding open top reservoir chambers 44 and 46 (chamber 44 having a fill line 45), and forwardly extending handle portion 48. A collection cup 50 is adapted to be frictionally secured on the underside of platform 16 in alignment with passage 22.

Further details of fractionation cartridge 40 may be seen with reference to FIGS. 2-6. Cartridge body 42 has a length of about four centimeters, a width of about two centimeters, and a thickness of about one-quarter centimeter. Body portion 42 includes an upper base plate 52, and a lower support plate 54 that have mating planar surfaces 56, 58 and which secure a filter membrane sheet 60 therebetween. Chambers 44 and 46 are molded integrally with upper base plate 52, and each has a height of about three centimeters and a cross-sectional area of about one square centimeter. Formed in the base of each chamber 44, 46 is a rectangular port 62, 64 respectively (best seen in FIG. 3), each of which has an area of about one-third square centimeter and is about one centimeter long. Formed in the lower surface of base plate 52 is a planar surface 66 that is recessed about 0.2 millimeter from reference surface 56 and that extends between ports 62 and 64. Recess 66 has a length of about 3½ centimeters and a width of about 1½ centimeters.

Lower support plate 54 has formed within the bounding planar upper surface 58 an array of twelve longitudinally extending parallel channels 68, each about 0.8 millimeter wide and 0.5 millimeter deep, that are spaced by support lands 70, each of which is about 0.2 millimeter in width. Transverse channel 72 (about one millimeter wide) provides flow communication between channels 68 and discharge passage 74.

The filter membrane 60 is a polycarbonate sheet that has a thickness of ten microns and a multiplicity of pores (the pore density being about $3 \times 10^7$ pores per square centimeter), the maximum pore size being 0.8 micron. Filter membrane 60 forms a planar lower surface of an elongated flow channel, the upper surface of which is defined by recess surface 66 such that the flow channel has a length of about 3½ centimeters, a width of about 1½ centimeters, and a height of about 0.2 millimeter. Members 52 and 54 are secured together (with membrane 60 positioned between them) by ultrasonic welding as indicated at 76 or other appropriate securing arrangement to form a sealed boundary about the flow channel.

Further details of the fractionation system may be seen with reference to FIGS. 7 and 8. Cartridge receiving structure 14 is mounted on housing 10 and projects forwardly from its front wall. Formed in the lower surface of platform 16 is an aperture 80 which is aligned with passage 22 and carries an O-ring 82 such that sample collection cup 50 may be inserted into and frictionally secured in aperture 80 in alignment with platform passage 22. The side and rear wall surfaces 18, 20 position cartridge 40 so that its collection passage 74 is aligned with platform passage 22.

Coupling plate 24 is shown in raised position in FIG. 7. That plate carries resilient sealing gaskets 26, each of which has a port 84 aligned with corresponding port 86 in coupling plate 24. A conduit connector 88 is threadedly received in each port 86 and has a corresponding conduit 28, 30 attached to it. Each such conduit extends rearwardly into housing 10 to a vent valve 100 and from that vent valve via coupling 102 to a pump chamber 104. Disposed within each pump chamber is a pump piston 106. The two pump pistons 106 are connected through drive linkage 108 of an alternating drive system that is powered by motor 110 for alternative reciprocation, one piston being withdrawn as the other piston is advanced, and vice versa, to alternately flow gas through conduits 28 and 30. In conjunction with each stroke, an interlock sensor 112 is triggered to close a vent valve 100 in one line, the valve 100 in the opposite line being open so that one conduit 28, 30 is always open to atmosphere.

Coupling plate 24 is moved between a raised position and a lower coupling position in which seal members 26 engage and seal the upper surfaces 114 of disposable cartridge 40 by an actuator linkage that includes drive motor 116, eccentric 118, and link rod 120. Rod 120 is connected to coupling plate 24 by lower disc 122 and by upper hemispherical member 124 which is biased downwardly against plate 24 by spring 126.

In operation of the system to obtain plasma from whole blood, with coupling plate 24 in raised position, a cartridge 40 with approximately 2½ milliliters of blood to be fractionated in chamber 44 (so that the level of blood is visible above line 45) is positioned on platform 16 so that its collection passage 74 is aligned with platform passage 22. When operating button 36 is depressed, motor 116 is operated to pull link rod 120 down and pivot coupling plate 24 so that seals 26 seat on and seal the upper surfaces 114 of reservoir chambers 44, 46. Motor 110 then operates the drive linkage 108 initially to advance piston 106A while withdrawing piston 106B to flow about two milliliters of blood from chamber 44 to chamber 46 through flow channel 66, vent valve 100B being open. When piston 106A has advanced a predetermined distance, vent valve 100A is opened and the actuation linkage is reversed to withdraw piston 106A while at the same time advancing piston 106B (and concurrently closing vent valve 100B). In each cycle, blood flows through channel 66 under a pressure of about two pounds per square inch at a rate of about one-half milliliter per second with air pressure being applied to the liquid blood surface and the reservoir not being emptied. The vent valves 100 are switched and the drive of pistons 106 is reversed after about one milliliter of blood has been flowed through channel 66 and operation is continued for ten cycles (a total blood volume displacement of about twenty milliliters). The system collects about one-half milliliter of plasma (with no visible hemolysis) in collection cup 50 in about one minute.

In summary, the operator need merely load reservoir chamber 44 of a cartridge 40 with the blood specimen to be fractionated (to fill line 45); then position the loaded cartridge 40 on platform 16, secure a collection cup 50 beneath platform 16, and push button 36. The system automatically couples the air flow system to reservoirs 44, 46, and then alternately applies air pressure to the surfaces of the blood in the reservoirs to produce gentle reciprocating flow of blood across filter membrane 60 (under the control of pistons 106 and vent valves 100 as indicated in FIG. 9) with the plasma component of the blood being flowed through membrane 60 to collection cup 50. The end of the one minute fractionation sequence is signalled by motor 116 automatically raising coupling plate 24. The operator then removes cartridge 40 and collection cup 50 which holds the collected plasma fraction; and may immediately insert another loaded cartridge 40 and another collection cup 50 and then press button 36 to initiate the next fractionation sequence.

Shown in FIG. 10 is another actuation arrangement in which compressed air is supplied through regulator 130, flow sensor 132 to and lines 134, 136 to three-way vent valves 138, 140. The vent valves are connected via conduits 28', 30' and coupling plate 24' to the plasma cartridge 40. Gas flow to reservoir chambers 44, 46 is alternated by control of vent valves 138, 140. A third actuation arrangement, shown in FIG. 11, includes drive motor 150 which reciprocates piston 152 in cylinder 154. Vent valves 156, 158 are connected to opposite ends of cylinder 154, as are conduits 28'' and 38''. Air is alternately flowed to reservoir chambers 44, 46 of cartridge 40 as piston 152 is reciprocated.

The following table summarizes results obtained with a fractionation cartridge of the type shown in FIGS. 2-6 in which the flow channel 66 had a length of about three centimeters, a width of about 1¼ centimeter and a depth of about 0.1 millimeter. In each fractionation run, one reservoir chamber was filled with approximately three milliliters of blood; the pressure was adjusted to the indicated level; and ten cycles of reciprocating blood flow through the fractionation channel, the flow direction being reversed after about one milliliter of blood had been displaced (a total blood volume displacement of twenty milliliters):

| Pressure (psig) | Time (seconds) | Volume of Plasma (milliliters) |
| --- | --- | --- |
| 6 | 14 | 0.4 |
| 5 | 13 | 0.5 |
| 4 | 20 | 0.45 |
| 4 | 17 | 0.4 |
| 3 | 30 | 0.6 |
| 3 | 27 | 0.4 |

In all cases no visible hemolysis of the plasma was observed.

The system gently produces smooth reciprocating liquid flow across a filtration membrane with low gas pressures that act on stable liquid surfaces. Handling of liquid specimens is facilitated by compact disposable filtration vessels. The system allows a filtered fraction of the liquid specimen to be obtained quickly and with minimal operator training and involvement in the processing sequence. While particular embodiments of the invention have been shown and described, various modifications will be apparent to those skilled in the art and therefore it is not intended that the invention be limited to the disclosed embodiments or to details thereof and departures may be made therefrom within the spirit and scope of the invention.

What is claimed is:

1. A fractionation system for fractionation of biological liquid material and the like comprising a filtration vessel that has a first reservoir chamber adapted to receive liquid material to be fractionated, a second reservoir chamber, a flow channel extending between and providing fluid communication between said reservoir chambers, one boundary of said flow channel being defined by a microporous membrane, and collection structure on the side of said membrane opposite said flow channel, means for providing gas pressure external of said reservoir chambers, substantially fluid tight coupling structure for connecting each said reservoir chamber to said means for providing gas pressure, and control means for communicating through said coupling structure said reservoir chambers alternately to said gas pressure providing means for providing application of gas pressure via said coupling structure alternately to said reservoir chambers for producing reciprocating flow of liquid material between said reservoir chambers through said flow channel for producing flow of a fraction of said liquid material through said membrane and into said collection structure.

2. The apparatus of claim 1 wherein said microporous membrane is a planar sheet that forms the lower boundary of said flow channel.

3. The apparatus of claim 2 wherein said flow channel forms the liquid material to be fractionated into a wide thin sheet, the depth of said flow channel being less than 0.3 millimeter, said flow channel having a width of at least twenty times its depth, and the volume of each said reservoir chamber being substantially greater than the volume of said flow channel.

4. The apparatus of claim 3 wherein said membrane has a multiplicity of pores, each said pore having a width dimension of less than one micron.

5. The apparatus of claim 1 wherein said gas pressure applying means is arranged to apply a gas pressure differential that does not exceed ten psi to said reservoir chambers.

6. The system of either claim 1 or 5 wherein said gas pressure applying means includes two gas flow conduits for connection to respective reservoir chambers, means to vent each said gas flow conduit to atmosphere, and means to operate said vent means alternately so that one reservoir chamber is vented to atmosphere whenever gas pressure is being applied to the other reservoir chamber through its gas flow conduit.

7. The system of either claim 1 or 5 and further including filtration vessel receiving structure and a fraction collection container for removable positioning adjacent said receiving structure, said filtration vessel being adapted to be removably positioned in said receiving structure in flow communication with said collection container.

8. The system of claim 7 wherein said filtration vessel coupling structure includes a coupling port at the top of each reservoir chamber, said coupling ports being disposed in a plane, and the top of one of said reservoir chambers is open for introduction of the liquid to be fractionated.

9. The system of claim 8 wherein said gas pressure applying means includes two gas flow conduits for connection to respective reservoir chambers, said gas pressure applying means being arranged to apply a gas pressure that does not exceed ten psi to the surface of liquid in each said reservoir chamber, means to vent each said gas flow conduit to atmosphere, and means to operate said vent means alternately so that one reservoir chamber is vented to atmosphere whenever gas pressure is being applied to the other reservoir chamber through its gas flow conduit, and further including releasable coupling structure for connecting said conduits to said reservoir chamber coupling ports.

10. The system of claim 9 wherein said flow channel forms the liquid material to be fractionated into a wide thin stream, and said microporous membrane is a planar member that forms the lower boundary of said flow channel, the depth of said flow channel being less than 0.3 millimeter, said flow channel having a width of at least twenty times its depth, and the volume of each said reservoir chamber being substantially greater than the volume of said flow channel.

11. A process for separating blood plasma from other components of whole blood without visible hemolysis comprising the steps of providing two spaced reservoir chambers that are connected by flow channel structure, said flow channel structure being bounded by filtration membrane structure that has a multiplicity of pores, the pores having a width dimension of less than one micron, disposing whole blood in said reservoirs and said flow channel so that a surface of the whole blood in each reservoir is exposed to gas, applying gas at a pressure not exceeding ten psi alternately to the exposed surfaces of the whole blood in said reservoir chambers to produce reciprocating flow of whole blood between said reservoir chambers through said flow channel structure with resulting flow of a plasma fraction free from visible hemolysis from said whole blood through said filtration membrane structure, and collecting said plasma fraction at a location below said membrane structure.

12. A system for fractionation of biological fluids and the like comprising a unitary disposable filtration vessel that has a first reservoir chamber adapted to receive liquid material to be fractionated, a second reservoir chamber, a flow port at the bottom of each said reservoir chamber, structure defining a flow channel extending between said reservoir chamber flow ports, microporous membrane structure defining a lower surface boundary of said flow channel, and filtrate collection structure below said membrane structure each said reservoir chamber being upwardly open and having a peripheral sealing surface at the open top of each chamber, support structure for receiving said filtration vessel including seat structure having a passage therethrough for alignment with said filtrate collection structure when said vessel is seated on said support structure, means for applying gas pressure to said reservoir chambers including coupling structure disposed above said support structure for sealing engagement with the sealing surface of each of said reservoir chambers, operating means for applying gas pressure through said coupling structure to the surface of liquid in said reservoir chambers, said operating means applying gas pressure to said chambers alternately for producing reciprocating flow of liquid material between said reservoir chambers through said flow channel with the resulting flow of a fraction of said liquid material through said membrane structure and said filtrate collection structure, and a filtrate collection container removably positioned adjacent said support structure in alignment with said filtrate collection structure for collecting the filtered fraction of liquid material that passes through said membrane structure.

13. The system of claim 12 and further including means to vent each said reservoir chamber and means to operate said vent means alternately so that each reservoir chamber is vented whenever gas pressure is being applied to the other reservoir chamber by said gas pressure applying means.

* * * * *